(12) United States Patent
Stewart

(10) Patent No.: US 6,374,828 B1
(45) Date of Patent: Apr. 23, 2002

(54) SINGLE WRAP, TWO-PLY REUSABLE SURGICAL WRAPPER

(75) Inventor: Richard F. Stewart, Mason, OH (US)

(73) Assignee: Standard Textile Co., Inc., Cincinnati, OH (US)

( * ) Notice: Subject to any disclaimer, the term of this patent is extended or adjusted under 35 U.S.C. 154(b) by 0 days.

(21) Appl. No.: 09/517,022

(22) Filed: Mar. 2, 2000

(51) Int. Cl.[7] .............................................. A61B 19/00
(52) U.S. Cl. ........................ 128/849; 428/340; 602/41
(58) Field of Search ................................ 128/849–856, 128/845, 846; 422/26, 34; 428/340; 602/41

(56) References Cited

U.S. PATENT DOCUMENTS

| | | | |
|---|---|---|---|
| 3,885,603 A | * | 5/1975 | Slaughter ................. 139/425 A |
| 4,301,206 A | | 11/1981 | Mills |
| 4,822,667 A | | 4/1989 | Goad et al. |
| 4,919,998 A | | 4/1990 | Goad et al. |
| 5,244,718 A | | 9/1993 | Taylor et al. |
| 5,635,134 A | | 6/1997 | Bourne et al. |
| 5,958,337 A | | 9/1999 | Bourne et al. |

OTHER PUBLICATIONS

Medline catalog pages showing surgical wrappers (two pages).
Best Mfg. catalog page showing surgical wrappers (one page).
One page showing Texture Shield, Fashion Blend, and Liquid Shield II wrappers.
Catalog sheet of StayTex and EviroTex surgical wrappers (one page).
Baxter Hospitex catalog sheets (two pages).
Angelica's Reusable Wrappers (one page).
Lintex product list (one page).
AORN online—Clinical Practice (printed on–line Nov. 16, 1999) (two pages).
*1999 Standards, Recommended Practices, and Guidelines*, "Recommended Practice for Surgical Attire" (pp. 183–188).
*1999 Standards, Recommended Practices, and Guidelines*, "Recommended Practices for Use and Selection of Barrier Materials for Surgical Gowns and Drapes" (pp. 245–248).
*1999 Standards, Recommended Practices, and Guidelines*, "Recommended Practices for Selection and Use of Packaging Systems" (pp. 277–282).
*1999 Standards, Recommended Practices, and Guidelines*, "Recommended Practices for Maintaining a Sterile Field" (pp. 317–322).
*Technical Report 68–41–CM*, "The Army Green Uniform", by Stephen J. Kennedy and Alice F. Park (Mar. 1968) (eighteen pages).

* cited by examiner

Primary Examiner—Michael A. Brown
(74) Attorney, Agent, or Firm—Wood Herron & Evans LLP

(57) ABSTRACT

Two plies (12, 14) woven from synthetic yarns (18) are joined together to define a single, two-ply surgical wrapper (10) which may be used to wrap a surgical pack (50) with only the single wrapper (10) to provide the effect of a sequential wrap.

27 Claims, 2 Drawing Sheets

SINGLE WRAP, TWO-PLY REUSABLE SURGICAL WRAPPER

BACKGROUND OF THE INVENTION

I. Field of the Invention

The present invention relates to reusable surgical wrappers, and more particularly, to such wrappers comprised of synthetic yarns to thus have inherent barrier properties.

II. Description of Prior Art

The use of surgical wrappers has become standard procedure to maintain sterility of surgical packs prior to use in the operating arena. To this end, a group of items to be used for a surgical procedure are assembled together as a so-called surgical pack. The surgical pack is then wrapped within fabric webs referred to as surgical wrappers, and sterilized. The sterilized and wrapped surgical pack is then available for use in a surgical procedure at which time the surgical wrappers are opened or removed exposing the surgical pack contents for use.

A reusable surgical wrapper is woven from yarns into a web and finished, such as with edge stitching, tape, marrowing, or serge stitching to produce a single surgical wrapper. Many surgical wrappers are woven from cotton or similar natural yarns and may be washed, dried and sterilized making them available for reuse. Unfortunately, wrappers manufactured with natural yarns do not inherently provide an adequate microbial or bacterial barrier and so it became the practice to wrap the surgical packs with not one single surgical wrapper, but with two separate single surgical wrappers in the hope of providing a sufficiently tortuous path that the surgical pack within would remain sterile. The process of utilizing two separate surgical wrappers became known as "sequential wrapping".

The use of all natural yarns for the surgical wrappers presented the additional problem of linting from the repeated washing and drying of the fabric. Lint is considered a contaminant in the operating arena and so is undesirable. Unfortunately, linting would often occur before the fabric has otherwise reached the end of its useful life, thereby leading to waste, as the linting surgical wrapper could no longer be reliably employed in the surgical arena. To reduce linting, some surgical wrappers are woven from cotton/polyester blended yarns. While linting is not entirely eliminated, the incidence of linting is delayed or reduced, thereby making available more of the useful life of the blended yarn surgical wrapper. Wrappers made of natural yarns or blended yarns are able to accept chemical treatments such as application of a barrier substance like Quarpel material. However, after repeated washing, drying and sterilization, the barrier properties are substantially lost from those wrappers. Moreover, the practice of sequential wrapping continues such that a plurality of single surgical wrappers were employed for each surgical pack.

Where all natural or blended yarns are used, a single wrapper may be comprised of a single ply of the woven yarn, or of two plies joined together along their peripheral edges. Even with the two-ply reusable single wrapper woven from natural or blended yarns, however, the practice of sequential wrapping continues.

A significant improvement was made with respect to reusable surgical wrappers by the introduction of single ply surgical wrappers woven primarily, if not completely, from synthetic yarns, rather than either natural yarns or blended yarns. Synthetic yarns provide a surgical wrapper that does not lint, and which also has an inherent barrier property to microbial and bacterial migration without adversely affecting the ability to sterilize the surgical wrapper. Moreover, the synthetic yarn provides the ability for the surgical wrapper to be repeatedly washed, dried and sterilized without substantially losing its inherent barrier properties. Notwithstanding that a barrier property was now present, the practice of sequentially wrapping a surgical pack using two separate or single surgical wrappers of one ply all synthetic yarn woven construction continues such that two of the synthetic yarn surgical wrappers are used to completely wrap a surgical pack.

SUMMARY OF THE INVENTION

An alternate approach to reusable surgical wrappers is the use of disposable surgical wrappers. Such disposable wrappers are not woven, but instead are nonwoven to be disposed of after a single use. Thus, it will be understood that as used herein, a nonwoven wrapper is generally recognized as being made from materials which cannot withstand repeated washing, drying and re-sterilization, whereas woven surgical wrappers are made from materials that are reusable after repeated washing, drying and sterilization. Even with disposable surgical wrappers, the concept of sequential wrapping is still employed such that two separate nonwoven web surgical wrappers would be wrapped around the surgical pack. One product introduced a few years ago bonds two different nonwoven webs together such as with adhesive or the like to create a two-ply nonwoven surgical wrapper which is said to provide the ability to "sequentially wrap" simply by wrapping the surgical pack with a single wrap of the two-ply disposable nonwoven wrapper. With reusables, however, the practice continues of using two identical, but separate surgical wrappers and sequentially wrapping the surgical pack.

The present invention provides an improved reusable surgical wrap and a method of using that surgical wrap which provides the effect of sequential wrapping with a single wrap, like that said to be obtained with the nonwoven surgical wrapper, but with reusable materials that are capable of being washed, dried and sterilized repeatedly without substantially adversely affecting or losing the barrier properties of the reusable surgical wrapper. To this end, and in accordance with principles of the present invention, two plies of woven synthetic yarns each having inherent barrier properties and adapted to be repeatedly washed, dried and sterilized without substantially losing the barrier properties, are joined together to provide a single, two-ply reusable surgical wrapper. The plies may be joined together by yarns such as with edge stitching, tape, marrowing or serge stitching, and/or by weaving yarns from one of the plies into the other so as to form an integral unit having interengaged plies. The two plies may be woven from identical yarns such that the plies are from the same woven material. The single surgical wrapper comprised of two interconnected plies of synthetic yarns is wrapped, as a single wrap, about a surgical pack while providing reliable and long lasting barrier properties as would otherwise have been accomplished with sequential wrapping. As a consequence, in a single wrap, the surgical pack is wrapped with the effect of two inherent barrier plies, much as would occur were two single, separate plies of the synthetic yarn surgical wrappers applied to the pack as a sequential wrap, but without the need to separately stack or sequentially wrap the two plies.

By virtue of the foregoing, there is thus provided an improved reusable surgical wrapper and a method of surgical wrapping to provide the effect of sequential wrapping without the need to use two or more single wrappers to wrap a surgical pack. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION OF THE DRAWINGS

Figure 1:
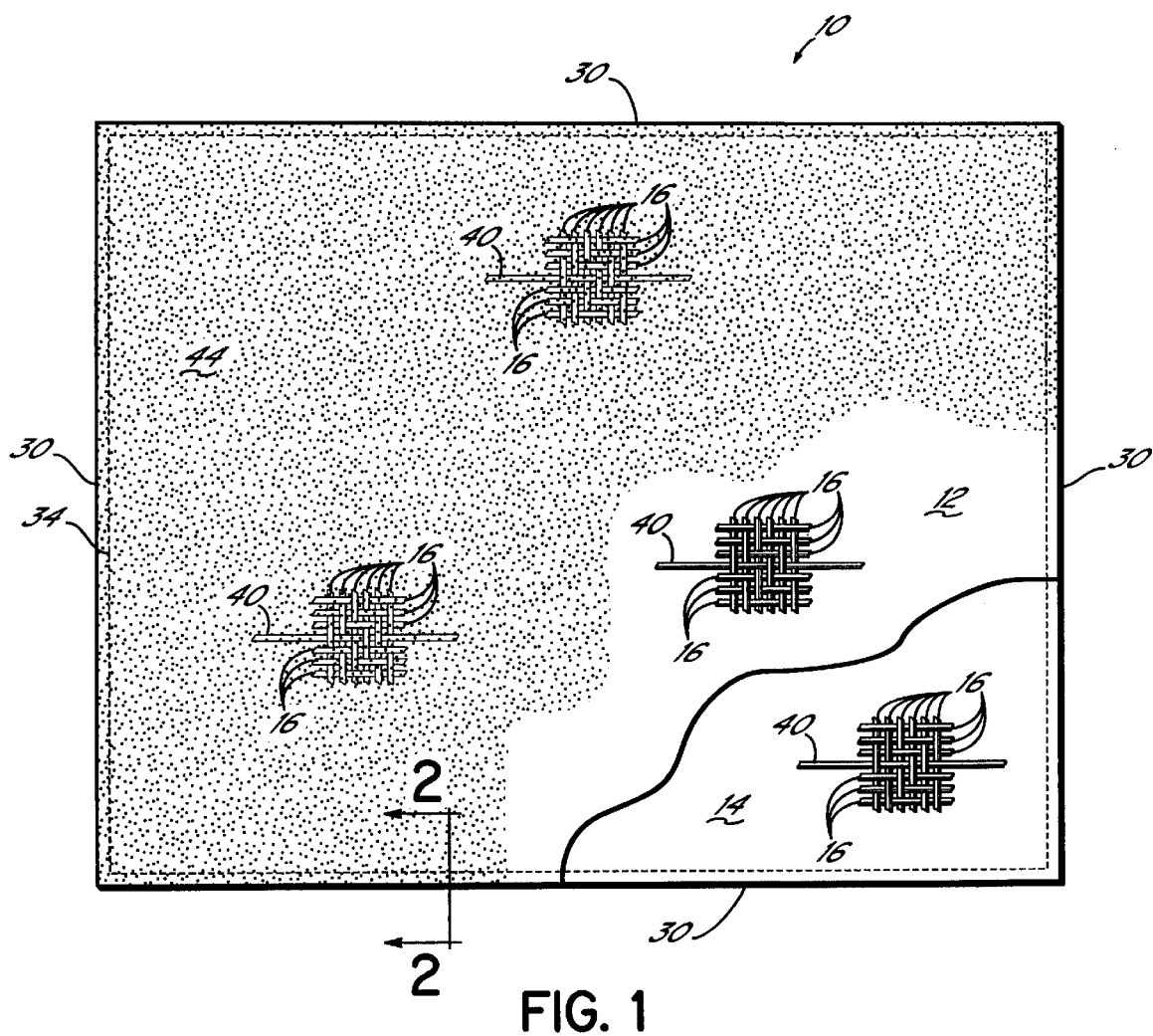
FIG. 1 is a perspective view, partially broken away, of one embodiment of a single surgical wrapper constructed in accordance with the principles of the present invention.

With reference to FIG. 1, there is shown a perspective view, partially broken away, of a single surgical wrapper 10 constructed in accordance with the principals of the present invention. Wrapper 10 includes two generally identifical plies or webs 12 and 14 each of which is woven essentially entirely of synthetic yarns 16 so as to be non-linting. Each web 12 or 14 may be comprised of a web of WrapPel-T surgical wrapper fabric marketed by Standard Textile Co., Inc., the assignee hereof. The construction of the WrapPel fabric may be as shown in U.S. Pat. No. 5,244,718, the disclosure of which is incorporated herein by reference in its entirety.

Figure 2:
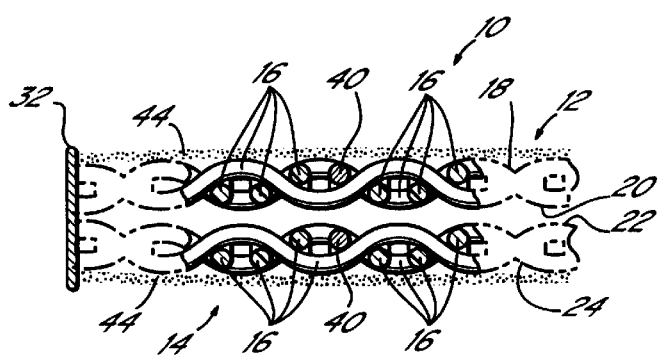
FIG. 2 is an exploded cross-sectional view along lines 2—2 of FIG. 1.

The two plies 12, 14 of fabric are of woven materials, i.e., they are reusable after repeated washing, drying and sterilization. Advantageously, the webs 12, 14 are woven essentially entirely of synthetic yarns 16 which are selected, and woven together with a denier and pick count selected, to provide the desired barrier properties, sterilization permeability, and "hand", as described in aforementioned U.S. Pat. No. 5,244,718, although a plain weave may be utilized if desired. To provide the effect of sequential wrapping, it is desirable to join together two webs 12, 14 in overlapping or confronting relationship as shown in FIG. 1. To this end, and with reference to FIG. 2, it will be seen that web 12 has an upper surface 18 and a lower, surface 20, while web 14 has an upper surface 22 and a lower surface 24. The webs 12 and 14 are generally thin enough that surfaces 18 and 20 on the one hand, and surfaces 22 and 24 on the other hand, may be considered to be generally parallel, notwithstanding the hills and valleys that may be present in woven or knitted fabrics. Webs 12 and 14 are placed one on top of the other with surface 20 of web 12 confronting and generally abutting surface 22 of web 14 (the webs are shown separated in FIG. 2, for ease of viewing, with the understanding that the webs will normally abut one another in use as a wrapper even though they may have gaps therebetween in places and may even puff apart such as during laundering), such that surfaces 18 and 24 define outer surface of wrapper 10. The adjacent peripheral edges 30 of webs 12, 14 are joined together such as with yarn 32 in conventional fabric joining fashion such as by marrowing or serge stitching as at 34 (FIG. 1). Yarn 32 could, alternatively, provide conventional edge stitching and be used with tape (both not shown). Yarn 32 may also be color-coded according to the size of wrapper.

Each web 12, 14 may further include woven therein one or more electrically conductive yarns 40, such as carbonaceous yarns as described in aforementioned U.S. Pat. No. 5,244,718, to reduce the incidence of electrostatic build-up of either of webs 12 or 14 or surgical wrapper 10. Also, either or both of webs 12 and 14, or yarns 16, may be coated or have otherwise applied thereto material 44 which enhances the performance of surgical wrapper 10. Such coatings may include antimicrobial, antistatic, liquid repellent or other materials readily recognized as useful in the surgical wrapper context. One such material may be a fluorocarbon water repellant such as disclosed in U.S. Pat. Nos. 4,822,667 and 4,919,998, the disclosures of both of which are incorporated herein by reference in their entireties. Where material 44 is applied, surfaces 18 and 24 are still considered as providing the outer surfaces of wrapper 10. Thus, surgical wrapper 10 is comprised of two plies, 12, 14 each of which consists essentially of woven synthetic yarns 16, and each having inherent barrier properties and adapted to be repeatedly washed, dried and sterilized without substantially losing the barrier properties. Webs 12 and 14 are joined together as at 34 to define a single surgical wrapper 10. It will be appreciated, that as used herein, "consists or consisting essentially of" or "essentially entirely of" means that the vast majority, if not substantially all, of the yarns used in the webs 12 and 14 are synthetic yarns having appropriate inherent barrier properties but which allow wrapper 10 to be repeatedly washed, dried and sterilized without substantially losing said barrier property. Those terms do not exclude the possibility of conductive yarns 40 woven therein, or materials 44 applied thereto, for example, which enhance the functions and features of wrapper 10. The terms are thus intended merely to exclude the presence as substantial parts of webs 12 or 14 any significant amount of either all natural or blended yarns which might create lint or loss of barrier properties as was characteristic of prior surgical wrappers, and to generally exclude the nonwoven materials which characterize the disposable surgical wrappers of the prior art.

Figure 3:
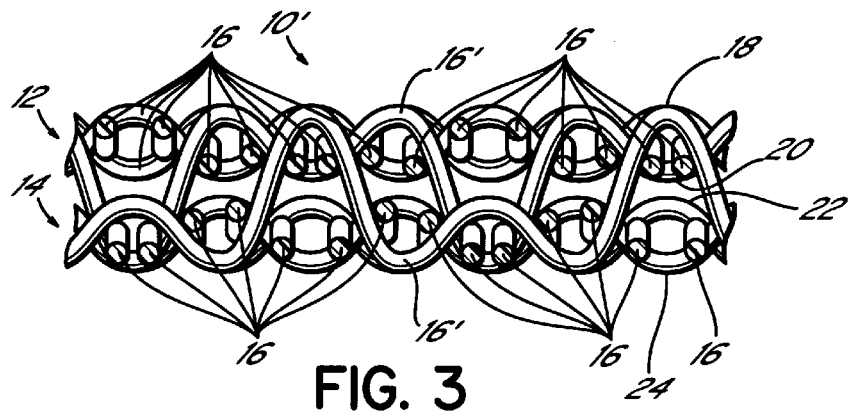
FIG. 3 is a cross-sectional schematic view of an alternate embodiment of a single, surgical wrapper constructed in accordance with the principles of the present invention.

Although plies 12 and 14 may generally be attached or joined along their peripheral edges 30, as at 34, they may alternatively or additionally be interengaged into an integral wrapper unit 10' (FIG. 3) such as during the weaving process. To this end, selected ones 16' of yarns 16 of web 12 and/or web 14 will extend beyond their respective surface 20 or 22 and into and beyond the opposite surfaces 22 and 20 to be woven into and with yarns 16 of web 14 and/or web 12, respectively, as exemplified in FIG. 3. The edge 30 may be narrowed or otherwise closed off with yarn 32 to prevent fraying and the like.

Figure 4:
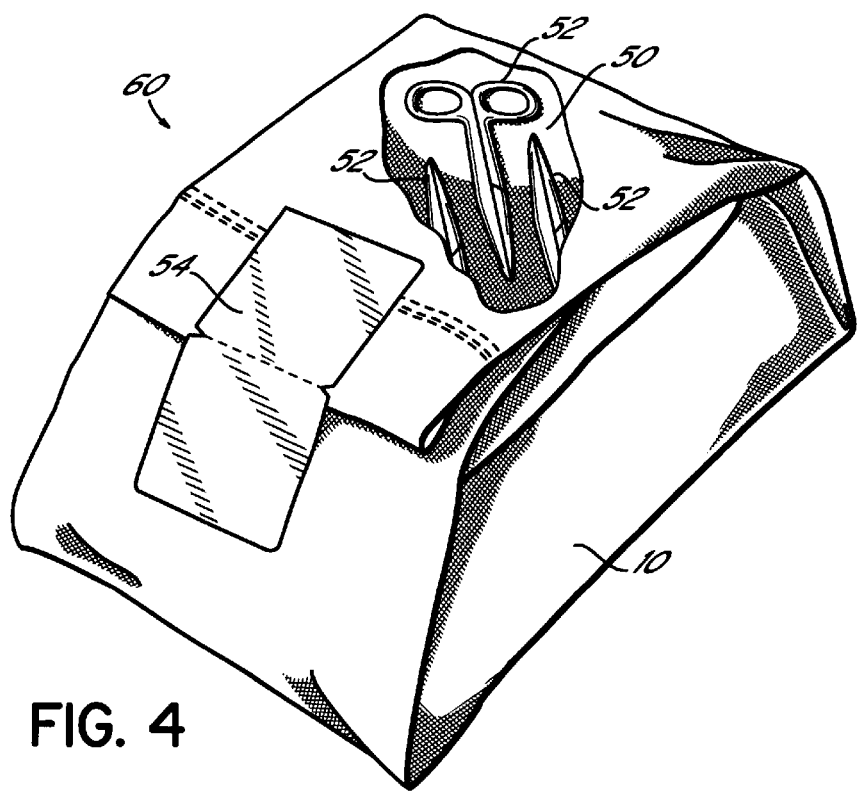
FIG. 4 is a perspective view, partially broken away, of a surgical pack wrapped in the single surgical wrapper of either FIG. 1 or FIG. 3.

In use, a single surgical wrapper 10 (or 10') is employed to wrap a surgical pack 50 as will now be described with reference to FIG. 4. To this end, the contents 52 of surgical pack 50 may be placed on a single surgical wrap 10, arid wrap 10 wrapped about surgical pack 50 as a single wrap. The single web may then be held closed by a tear-open sealing tape 54 to provide a completed product 60 comprised of the surgical pack 50 and its contents 52 and a single surgical wrapper 10, without the need for any other surgical wrappers or other such wrappers. As a consequence, it is unnecessary to utilize a second surgical wrapper 10 thereby providing the effect of two plies 12, 14 of reusable, inherent barrier surgical wrapper material without the need for an operator to separately collect the two plies 12 and 14 each time a pack 50 is to be wrapped. Moreover, there are advantages in the laundering process in that the wrapper 10 or 10' is essentially non-linting and in that the two plies 12, 14 are interconnected together more or less permanently and so may be washed as a single unit. Consequently, the separate handling of plies 12 and 14 during the laundering and sterilization process is not required.

To access pack 50 and its contents 52, tape 54 is broken or torn, and wrapper 10 laid out to reveal the contents 52.

By virtue of the foregoing, there is thus provided an improved reusable surgical wrapper and a method of surgical wrapping to provide the effect of sequential wrapping without the need to use two or more single wrappers to wrap a surgical pack.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while webs 12 and 14 are advantageously identical, they need not be. They could be made from different synthetic yarns, or from different denier or with different pick count of yarns. In this regard, and to further reduce laundry costs, the denier and/or pick count of yarns 16 in both webs 12 and 14 may be reduced to lessen the overall weight of wrapper 10. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A two-ply reusable surgical wrapper having barrier properties and which is to be washed, dried and sterilized subsequent to each use, and which is adapted to provide in each use the effect of sequential wrapping with two separate plies in a single wrapper, comprising:
   a first ply consisting essentially of woven synthetic yarns, the first ply having barrier properties and adapted to be repeatedly washed, dried and sterilized without substantially losing said barrier properties, the first ply defining an upper surface and a lower, generally parallel surface;
   a second ply consisting essentially of woven synthetic yarns, the second ply having barrier properties and adapted to be repeatedly washed, dried and sterilized without substantially losing said barrier properties, the second ply defining an upper surface and a lower, generally parallel surface; and
   yarn joining the first and second barrier plies together with the lower surface of the first ply and the upper surface of the second ply being in confronting and generally abutting relationship such that the upper surface of the first ply defines an outer surface of the surgical wrapper and the lower surface of the second ply defines another outer surface of the surgical wrapper, whereby wrapping a surgical pack with the surgical wrapper provides the effect of sequential wrapping with two separate plies.

2. The surgical wrapper of claim 1, at least one of the plies including conductive yarn woven therein.

3. The surgical wrapper of claim 1, each of the plies including conductive yarns woven therein.

4. The surgical wrapper of claim 1 wherein each of the plies includes peripheral edges, the peripheral edges of the first ply being adjacent the peripheral edges of the second ply, the yarn joining the plies including stitching along adjacent peripheral edges.

5. The surgical wrapper of claim 1 wherein the yarn joining the plies includes marrowing.

6. The surgical wrapper of claim 1, the yarn joining the plies including selected ones of the yarns of the first ply being woven into the second ply.

7. The surgical wrapper of claim 1, the yarn joining the plies including selected ones of the yarns of the second ply being woven into the first ply.

8. The surgical wrapper of claim 1, the yarn joining the plies including selected ones of the yarns of each of the first and second plies being woven into the second and first plies, respectively.

9. The surgical wrapper of claim 1 including a material treatment.

10. The surgical wrapper of claim 1, the material treatment including fluorocarbon.

11. The surgical wrapper of claim 1, the first and second plies being woven from generally identical synthetic yarns.

12. A method of single wrapping a surgical pack comprising:
   forming a single, reusable surgical wrapper which is adapted to be washed, dried and sterilized subsequent to each use, forming the wrapper including:
      weaving synthetic yarns into a first barrier ply having an upper surface and a lower, generally parallel surface;
      weaving synthetic yarns into a second barrier ply having an upper surface and a lower, generally parallel surface; and
      joining the first and second barrier plies together with the lower surface of the first barrier ply and the upper surface of the second barrier ply being in confronting and generally abutting relationship such that the upper surface of the first barrier ply defines an outer surface of the surgical wrapper and the lower surface of the second barrier ply defines another outer surface of the surgical wrapper; and
   wrapping a surgical pack with the single, surgical barrier as a single wrapper.

13. The method of claim 12 further comprising joining the first and second plies together with yarn.

14. The method of claim 12 wherein joining the first and second plies together includes stitching respective edges thereof together.

15. The method of claim 12 wherein joining the first and second plies together includes marrowing.

16. The method of claim 12 wherein joining the first and second plies together includes weaving selected yarns of the first ply into the second ply.

17. The method of claim 12 wherein joining the first and second plies together includes weaving selected yarns of the second ply into the first ply.

18. The method of claim 12 wherein joining the first and second plies together includes weaving selected yarns of the first and second plies into the second and first plies, respectively.

19. The method of claim 12 further comprising treating the wrapper with a material.

20. The method of claim 19 wherein treating the wrapper includes treating the yarns thereof.

21. The method of claim 19 wherein treating the wrapper includes treating the wrapper with fluorocarbon.

22. The method of claim 12 further comprising weaving the first and second plies from generally identical synthetic yarns.

23. The method of claim 12 further comprising weaving conductive yarns into at least one of the plies.

24. A two-ply reusable surgical wrapper having barrier properties and which is to be washed, dried and sterilized subsequent to each use, and which is adapted to provide in each use the effect of sequential wrapping with two separate plies in a single wrapper, comprising:

a pair of plies each consisting essentially of woven synthetic yarns, the plies having barrier properties and adapted to be repeatedly washed, dried and sterilized without substantially losing said barrier properties, the plies being in overlapping relationship to define a pair of opposed outer surfaces; and yarn joining the plies together such that the opposed outer surfaces define upper and lower surfaces of the surgical wrapper, whereby wrapping a surgical pack with the surgical wrapper provides the effect of sequential wrapping with two separate plies.

25. A two-ply reusable surgical wrapper having barrier properties and which is to be washed, dried and sterilized subsequent to each use, and which is adapted to provide in each use the effect of sequential wrapping with two separate plies in a single wrapper, comprising:

a pair of woven plies each being essentially non-linting, having barrier properties and adapted to be repeatedly washed, dried and sterilized without substantially losing said barrier properties, the plies being in overlapping relationship to define a pair of opposed outer surfaces; and yarn joining the plies together such that the opposed outer surfaces define upper and lower surfaces of the surgical wrapper, whereby wrapping a surgical pack with the surgical wrapper provides the effect of sequential wrapping with two separate plies.

26. A method of single wrapping a surgical pack comprising:

forming a single, reusable surgical wrapper which is adapted to be washed, dried and sterilized subsequent to each use, forming the wrapper including:

weaving synthetic yarns into a pair of overlapping barrier plies and defining a pair of opposed outer surfaces; and joining the barrier plies together with the opposed outer surfaces defining upper and lower surfaces of the surgical wrapper; and wrapping a surgical pack with the single, surgical barrier as a single wrapper.

27. A method of single wrapping a surgical pack comprising:

forming a single, reusable surgical wrapper which is adapted to be washed, dried and sterilized subsequent to each use, forming the wrapper including:

forming a pair of non-linting, woven, overlapping barrier plies and defining a pair of opposed outer surfaces; and joining the barrier plies together with the opposed outer surfaces defining upper and lower surfaces of the surgical wrapper; and wrapping a surgical pack with the single, surgical barrier as a single wrapper.

* * * * *